United States Patent [19]
Heddle et al.

[11] Patent Number: 5,968,773
[45] Date of Patent: Oct. 19, 1999

[54] SYSTEM AND METHOD FOR REGULATION OF GENE EXPRESSION

[76] Inventors: John A. Heddle, 11975 Kipling Avenue, Kleinburg, Ontario, Canada, L0J 1C0; Roy R. Swiger, 4 Oldfield Street, Maple, Ontario, Canada, L6A 1R8

[21] Appl. No.: 08/970,315

[22] Filed: Nov. 14, 1997

[51] Int. Cl.$^6$ .............. C12P 21/02; C12N 5/10; C12N 15/10; C12N 15/11
[52] U.S. Cl. .............. 435/69.1; 435/320.1; 435/325; 435/375; 435/410; 536/23.1; 536/23.2
[58] Field of Search ................ 536/23.1, 23.2, 536/23.4, 24.1, 23.5, 23.7; 435/325, 410, 243, 320.1, 69.1, 375

[56] References Cited

U.S. PATENT DOCUMENTS

| | | | |
|---|---|---|---|
| 5,347,075 | 9/1994 | Sorge | 800/18 |
| 5,464,758 | 11/1995 | Gossen et al. | 435/69.1 |
| 5,510,099 | 4/1996 | Short et al. | 800/3 |
| 5,589,392 | 12/1996 | Short | 435/320.1 |

FOREIGN PATENT DOCUMENTS

| | | |
|---|---|---|
| 9404672 | 3/1994 | WIPO . |
| 9601313 | 1/1996 | WIPO . |
| 9640892 | 12/1996 | WIPO . |
| 9735992 | 10/1997 | WIPO . |

OTHER PUBLICATIONS

Swiger, Roy R. et al. "A beta galactosidase reporter vector for mammalian cell lines," Environmental and Molecular Mutagenesis (1998) Vol. 31 No. Suppl 29 p. 28.

Baron V., et al. "Co–regulation of Two Gene Activities by Tetracycline via a Bidirectional Promoter," Nucleic Acids Research, vol. 23 No. 17, Sep. 11, 1995, page 3605/3606.

Deuschle V. et al. "Tetracycline–Reversible silencing of Eukaryotic Promoters", Molecular and Cellular Biology, vol. 15, No. Apr. 4, 1995 pp. 1907–1914.

Park, 1994 DNA and Cell Biology, vol. 13, No. 11; A β–Galactosidase Expression Vector for Promoter Analysis.

Gossen et al. Oct. 1989 *Proc. Natl. Acad. Sci. USA*, vol. 86, pp. 7971–7975; Efficient rescue of integrated shuttle vectors from transgenic mice: A model for studying mutations in vivo.

Kolher, et al. Sep. 1991 *Proc. Natl. Acad. Sci. USA*, Vol. 88, pp. 7958–7962; Spectra of spontaneous and mutagen–induced mutations in the *lacI* gene in transgenic mice.

Gossen et al. Jun. 1992 *Proc. Natl. Acad. Sci. USA*, vol. 89, pp. 5547–5551; Tight control of gene expression in mammalian cells by tetracycline–responsive promoters.

Furth, et al. Sep. 1994 *Proc. Natl. Acad. Sci. USA*, vol. 91, pp. 9302–9306; Temporal control of gene expression in transgenic mice by a tetracycline–responsive promoter.

Deuschler, et al. Apr. 1995 Molecular and Cellular Biology, pp. 1907–1914; Tetracycline–Reversible Silencing of Eukaryotic Promoters.

*Primary Examiner*—Terry McKelvey
*Attorney, Agent, or Firm*—Merchant & Gould P.C.

[57] ABSTRACT

The present invention provides a polynucleotide molecule coding for a protein operably linked to a tet operator sequence and at least two promoters. Preferably, the polynucleotide molecule is operably linked to a transrepressor fusion protein comprising a tet repressor and a transcription silencer protein domain.

17 Claims, 3 Drawing Sheets

FIG. I

SYSTEM AND METHOD FOR REGULATION OF GENE EXPRESSION

BACKGROUND OF THE INVENTION

1. Field of the Invention

The present invention relates to the field of gene expression. More specifically, the invention relates to a system and method for regulating gene expression.

2. Description of the Prior Art

The bacterial β-galactosidase gene (lacZ) is an excellent reporter gene and is used extensively in life science applications including: cloning (Sambrook et al., 1989. *Molecular Cloning: A Laboratory Manual*, $2^{nd}$ ed. Cold Spring Harbor Laboratory Press, Plainview, N.Y.); promoter assessment (Park et al., 1994. A β-galactosidase Expression vector for promoter analysis. *DNA and Cell Biology*. 13:1147–1149.); gene regulation and function; and mutation analysis (Gossen et al. 1989. Efficient rescue of integrated shuttle vectors from transgenic mice: a model for studying mutations in vivo. *Proc. Natl. Acad. Sci.* 86: 7981–7985). lacZ provides straightforward results regarding expression and function upon chromogenic assays using the substrate X-gal or ONPG; the quantitation of the protein is easily and reliably attained upon cell lysis, staining and spectrophotometric analysis; and the detection of in-vivo expression of the lacZ in mammalian cells is easily accomplished using basic histochemical staining.

It is of interest to have a reporter whereby transcription may be experimentally controlled. Although many eukaryotic promoters have been identified and cloned, they are often leaky (i.e., they do not provide total on-off control) and/or lack responsiveness in mammalian cell lines. Moreover, the inducers are generally deleterious to the host cell or have significant drawbacks such as toxicity.

Many chimeric transcription factors have been developed in order to ameliorate these problems. Earlier attempts at producing chimeric transcription factors were based on using the glucocorticoid receptor (Baniahmad et al., 1993. Mechanisms of transcriptional activation by steroid hormone receptors. *J Cell Biochem*. 51: 151–6). More recently the bacterial lac and tet operons have been exploited. The lac based systems have been characterised as "leaky" whereas the tet-based binary systems have exhibited greater fidelity between protein and operator sequences. Additionally, the tet-based systems are inducible using tetracycline, a well known and well characterised compound.

Two tetracycline responsive binary systems have been previously described (Deuschle et al., 1995. Tetracycline-reversible silencing of eukaryotic promoters, *Molecular and Cellular Biology*. 15: 1907–1914; and Gossen and Bujard, 1992. Tight control of gene expression in mammalian cells by tetracycline-responsive promoters. *Proc. Natl. Acad. Sci. USA*. 89: 5547–5551, the contents of both of which are incorporated herein by reference.). Both the Deuschle and the Gossen and Bujard systems utilize a cis regulatory sequence composed of a heptameric repeat of the tetracycline operator (tetO) 19 bp inverted repeat fused to the immediate early sequences of the cytomegaloviral enhancer (TetO7CMV). However, the chimeric transcription factors are quite different. The tetracycline-controlled transactivator (tTA) system of Gossen and Bujard is composed of the tetR protein fused to the transactivating carboxy terminus of the VP-16 protein. The tetRKRAB chimera of Deuschle consists of the highly conserved KRAB (Kruppel-associated box) domain of the Kox1 Zn-finger protein family fused to the tetracycline repressor protein (tetRKRAB).

Accordingly, the motifs differ in their kinetics and mechanism of protein-DNA associations. The tTA system is induced by the absence of tetracycline. In the uninduced state however basal levels of expression tend to be relatively high due to the CMV sequences. The tetRKRAB system makes use of the transcriptional silencing influence of the KRAB domain. This system maintains much lower levels of basal activity in the repressed state, and is induced by the addition of tetracycline. Nevertheless, to date, induction levels are much lower than that observed in the tTA.

It is an object of the present invention to obviate and mitigate at least one of the disadvantages of conventional gene expression regulatory systems.

SUMMARY OF THE INVENTION

Accordingly, in one of its aspects, the present invention provides a polynucleotide molecule coding for a protein operably linked to a tet operator sequence and at least two promoters.

Preferably, the polynucleotide molecule is operably linked to a transrepressor fusion protein comprising a tet repressor and a transcription silencer protein domain.

Also preferably, the polynucleotide molecule is a reporter gene selected from the group comprising: bacterial β-galactosidase gene (lacZ), CAT-chloramphenicol transferase reporter, luciferase reporter and Green Fluorescent Protein, and the promoters are selected from the group comprising: human cytomegalovirus promoter, SV-40 early or late promoter, Epstein-Barr Virus promoter and Baculovirus.

In another aspect, the present invention provides a eucaryotic cell transfected with:

(a) a first polynucleotide molecule coding for a protein operably linked to a tet operator sequence and at least two promoters; and (b) a second polynucleotide molecule coding for a transrepressor fusion protein comprising a tet repressor and a transcription silencer protein domain.

In yet another aspect, the present invention provides a kit comprising at least two containers, the first container containing a polynucleotide molecule coding for a transrepressor fusion protein comprising a tet repressor and a transcription silencer protein domain, the second container containing a polynucleotide molecule comprising a tet operator sequence and at least two promoters, wherein at least one of the at least two promoters is capable of being ligated to a gene sequence coding for a protein.

BRIEF DESCRIPTION OF THE DRAWINGS

A preferred embodiment of the present invention will be described, by way of example only, with reference to the accompanying drawings, in which.

DETAILED DESCRIPTION OF THE PREFERRED EMBODIMENT

In the following description, a number of recombinant DNA technology terms are used. The following definitions have been provided in order to provide a clear understanding of the specification and appended claims:

"Promoter"—a DNA sequence generally described as the 5' region of a gene, located proximal to the start codon. The transcription of an adjacent gene is initiated at the promoter region. If a promoter is an inducible promoter then the rate of transcription increases in response to an inducing agent.

"Minimal Promoter"—a partial promoter sequence which defines the transcription start site but which by itself is not capable of initiating transcription efficiently. The activity of minimal promoters depends on the binding of activators to operably linked binding sites.

"Operably Linked"—a nucleic acid sequence is "operably linked" when placed into a functional relationship with another nucleic acid sequence. For instance, a promoter or enhancer is "operably linked" to a coding sequence if the promoter causes the transcription of the sequence. Generally, operably linked means that the DNA sequences being linked are contiguous and, where necessary to join two protein coding regions, contiguous and in reading frame.

"Gene"—a DNA sequence that contains information needed for expressing a polypeptide or protein.

"Reporter Gene"—a gene used to indicate functional expression and/or which is easily identified using conventional detection methods.

"Polynucleotide Molecule"—a polydeoxyribonucleic acid molecule (DNA) or a polyribonucleic acid molecule (RNA).

"Expression"—the process by which a polypeptide is produced from a structural gene.

"Tetracycline Analogue"—any one of a number of compounds that are closely related to tetracycline and which bind to the tet repressor (tetR)

Figure 1:
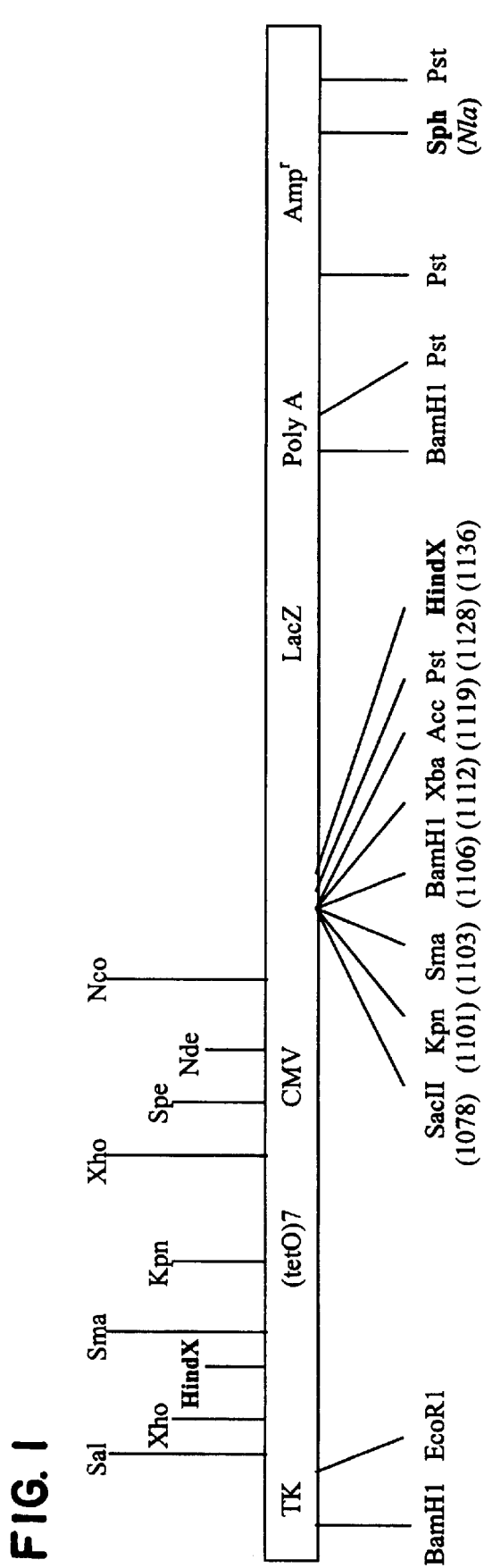
FIG. 1 is a restriction map of an operator sequence in accordance with a preferred embodiment.

A polynucleotide molecule coding for a protein operably linked to a tet operator sequence and at least two promoters in accordance with one embodiment of the present invention is shown in FIG. 1. The TK(tetO)7CMV-lacZ reporter plasmid is tetracycline-responsive when transfected with an expression vector coding for the chimeric trans-repressing protein (tetRKRAB). This reporter construct contains an upstream thymidine kinase minimal promoter (TK) of the herpes simplex virus, followed by a regulatory cis element composed of a heptameric tet-operator (tetO7) from the tetracycline-resistance operon encoded in Tn10 E. coli, combined with the immediate early sequences from the cytomegaloviral (CMV) enhancer.

The reporter plasmid was constructed in accordance with the following methodology.

TK-tetO7CMV-LacZ Construction

The parent vector of the reporter, pCH110 (Pharmacia Biotech Inc., Piscataway, N.J.) was modified as described in Park et al. referred to above, the contents of which are incorporated herein by reference. The vector pTKβgal is a pBR322 vector containing a unique Sph1 site upstream from a TK minimal promoter, flanked by the multiple cloning sites, followed by the β-galactosidase gene.

The ptetO7-CMV-luc and the pCMV-tetR-KRAB expression vectors used were as described in Deuschle et al. referred to above. The construct containing the tetO7-CMV operator was used as a template for the polymerase chain reaction (PCR). The upstream primer, 2HU introduces a HindIII restriction site (shown underlined); 5' ACG AGG CCC TTT AAG CTT CAA GAA TTC CTC 3' (SEQ ID NO:1). The downstream primer 1HD sequence incorporated the existing HindIII site in the template (ptetO7-CMV-luc); 5' CAG TAC CGG AAT GCC AAG CTT GCA 3' (SEQ ID NO: 2). The tetO7-CMV 1.3 Kb PCR fragment was digested with HindIII and inserted at the HindIII site downstream of the TK minimal promoter, yielding the lacZ reporter TKtetO7CMV/acZ (FIG. 1).

Figure 2:
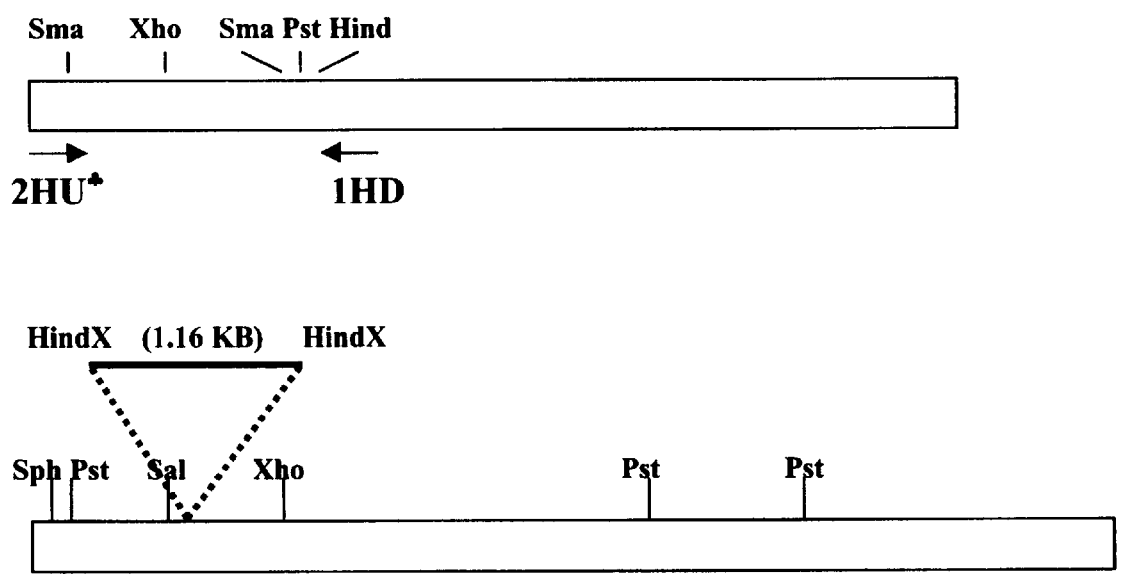
FIG. 2 is a representation of the cloning of the operator sequence of FIG. 1.

FIG. 2 shows the cloning of TK(tetO)7CMVlacZ. The heptameric (tetO)7CMV cis sequence from ptetO7-CMV-luc was PCR amplified with primers which introduced an upstream HindIII site (1HU) and incorporated a downstream HindIII site (2HD). The products, the 1.2Kb operator region was flanked by HindIII, were then inserted into the HindIII site of the MCS in pTKlacZ.

Because the upstream HindIII site was introduced, the annealing temperature was lowered for the first 6 rounds of PCR. PCR profiles were as follows: 94° C., 30 sec; 59° C., 1.5 min; 72° C., 30 sec for 6 rounds followed by 25 rounds with the standard PCR profile 94° C., 62° C., 72° C. for 30 sec, 1.5 min, 30 sec respectively.

Cell Culture and Lipofection

HeLa cell lines were cultured in Iscoves modified Dulbecco's Minimal Eagles Medium (DMEM) (Life Technologies, Inc., Gaithersburg, Md.) supplemented with 5% fetal bovine serum (Summit Biotechnology, Fort Collins, Colo.), penicillin-streptomycin (Life Technologies, Inc.) and fungizone. Cells were seeded at roughly $11.5 \times 10^5$ cells per 60mm petri-dish and were incubated overnight to roughly 70–80% confluency. DNA used in the transfection experiments consisted of PCR products using primers that flanked the entire ORF or purified plasmids from DH5αMaxEfficiency hosts (Life Technologies, Inc., Gaithersburg, Md.), using the Qiagen midi prep protocol (Qiagen Inc., Chatsworth, Va.). DNA was transfected using Lipofectamine (Life Technologies, Inc., Gaithersburg, Md.) and a 4:1 ratio of DNA::CMV-tetR-KRAB: TK-tetO7CMV-lacZ. Roughly 2.5 µg of DNA was combined with serum free media to a volume of 160 µL which was then combined with 7–9 µL of Lipofectamine in 160 µL serum free media. Approximately 2 µg of the SV-40 driven β-galactosidase expression vector pCH110 (Pharmacia Biotech Inc., Piscataway, N.J.) was used as a positive control. The cultures were washed and provided fresh media 4-5 hours after transfection. In order to induce expression, media containing subinhibitory levels of tetracycline (0.5 µg/ml) was added to some cultures.

Assay for β-Galactosidase Activity

β-galactosidase activity was measured using the β-galactosidase assay kit (Stratagene, La Jolla, Calif.) and o-nitrophenyl-β-D-galactopyranoside (ONPG). Briefly, cells were washed with phosphate buffered saline (PBS), lysed with a mild detergent and supernatants were collected. Cell extracts were analyzed by spectrophotometric measurements, $OD_{420}$. All samples were normalized using Lowry staining (Bio-Rad, Hercules, Calif.). In order to reduce endogenous mammalian β-galactosidase, samples were soaked at 44° C. for 50 minutes before addition of ONPG.

The tetR-KRAB binary system of the prior art described by U. Deuschle is extremely reliable in the repression of activity but is far less inducible when compared to the tTA binary system described by Gossen and Bujard. By placing the (tetO)7CMV downstream of the TK and upstream of the lacZ in the present invention, the inventors have found that, in the repressed state, TK promotion appears to be inhibited by the bulky tetR-KRAB complexes. However, when the complexes are destabilized by the addition of tetracycline, the TK and CMV promotion display synergism. In transiently transfected HeLa cells, induction is well in excess of 100 fold.

By combining the CMV and TK promotion, the system and method of the present invention provide: i) a much quicker response to tetracycline addition; and ii) a much higher induction overall, by as much as 25 times that observed for tetO7CMV reporters lacking the upstream TK promoter when transfected with the tetRKRAB construct Additionally, the excellent repression of the tetR-KRAB has not been compromised.

Figure 3:
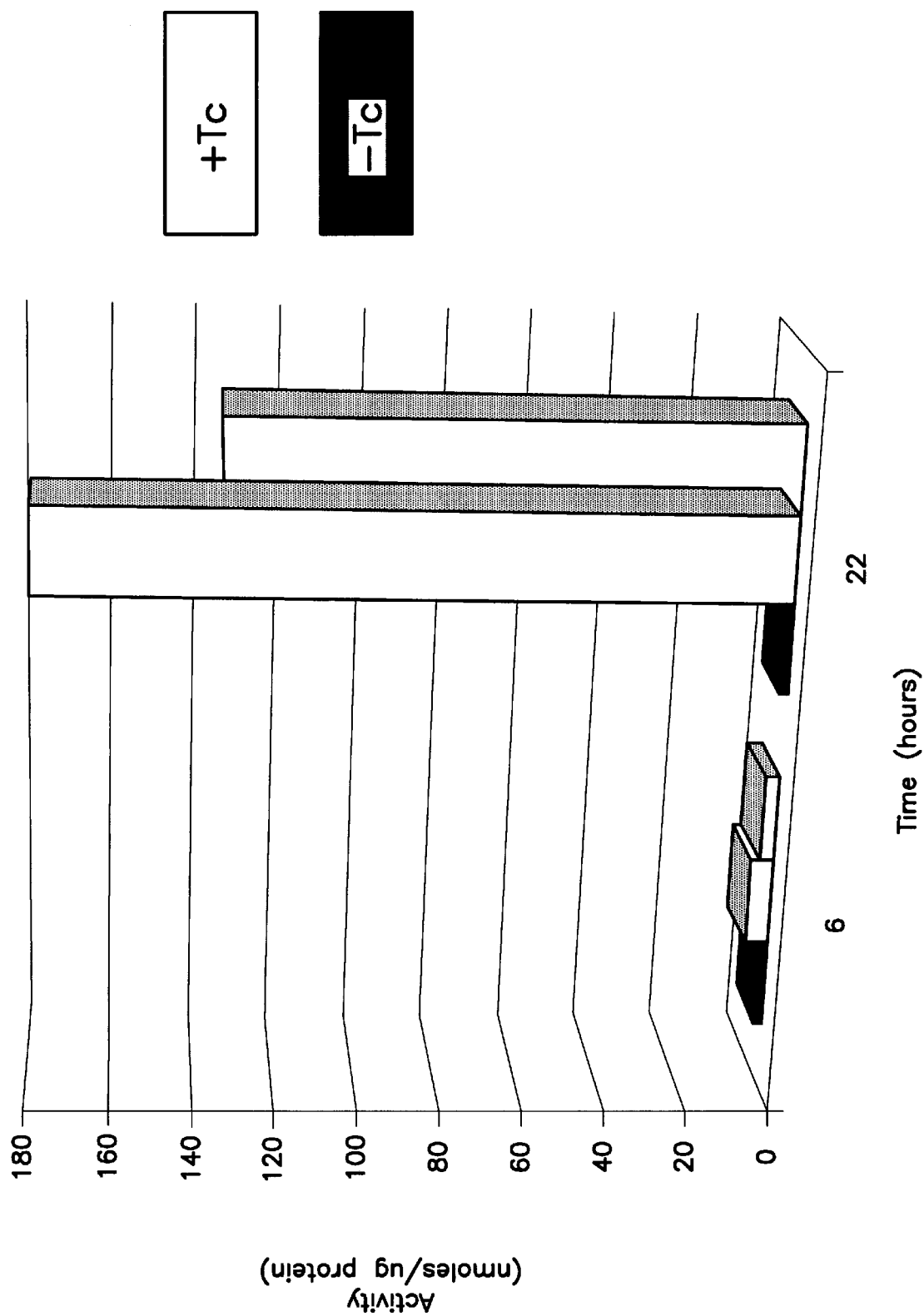
FIG. 3 shows the tetracycline-responsiveness of transiently transfected HeLa cells over time.

FIG. 3 shows the tetracycline-responsiveness of transiently transfected HeLa cells over time. Tetracycline (0.5 ug/ml) was added to two of three transfected cultures in order to observe differences in transfection efficiency, one culture was maintained without Tc. The cells were grown in 60 mm diameter petri plates, transfected at 80% confluency and were not split throughout the experiment.

As shown in FIG. 3, upon transient transfection of the reporter (plasmid or PCR products) with the ptetRKRAB, high levels of induction are reached by 22 hours after addition of tetracycline. Levels of induction are in the range of 50–300+ fold usually by hour 19 (data not shown). In one particular experiment extremely high levels of induction (>100 fold) were reached by 9.5 hours after transfection. In most cases however, by hour(s) 6–9, induction levels are within the range of 10-fold.

The reproducibility and efficacy of this system will be subject to host cell line, integration site and investigator variances. Notably, BHK and Vero cell lines have been shown to display from 10 to 580 fold higher levels of induction than HeLa and PC12 lines using the tetO7CMV operator and the tTA transactivating protein (Acklund-Berglund et al, Efficacy of tetracycline-controlled gene expression is influenced by cell type, *Biotechniques*, 18:196–200 (1995)). Other tetR fusion proteins should also recognize the reporter vector of the present invention. It is contemplated that the use of the tetR-VP 16 transactivating protein and TK-tetO7CMV-lacZ will result in an inverse pattern of induction relative to tetracycline.

Because the origins of the chimeric factor include the KRAB repression domain, which is highly conserved amongst mammals, possible non-specific interaction with other cis-sequences may occur. Such predicted interactions have been observed in the tTA system.

Cell lines expressing tetR-KRAB and/or TK-tetO7CMV-lacZ constructs using cotransfection with a neomycin expression vector, pMAMneo (Clonetech, Palo Alto, Calif.) have been constructed.

In another embodiment, it is envisioned that both promoters may be placed on the same "side" of the tet operator sequence, i.e., both promoters may be upstream of the tet operator or both promoters may be downstream.

Although the present invention has been described with reference to a construct having a TK promoter in conjunction with a CMV promoter, it will be apparent to a person of skill in the art that other promoter sequences could be used.

For example, one or both of the promoters could be substituted by Simian Virus 40 (SV-40) early or late promoter, Epstein-Barr Virus promoter or Baculovirus promoter. These promoters are all described in the literature and the readers attention is directed to, for example, S. Mongkolsuk, *Gene*, 70 (1988) 313, J. Sambrook et al., "Molecular Cloning" (1989) Cold Spring Harbor Laboratory, Cold Spring Harbor, N.Y., and S. E. Hasnain et al., *Gene*, 190(1) (1997) 113, the contents of each of which are incorporated herein by reference.

Further, it will be apparent to a person of skill in the art that the promoter-operator-promoter construct need not necessarily only be used in conjunction with lacZ reporter gene. Other suitable reporter genes include the CAT-chloramphenicol transferase reporter (see, for example, J. H. Miller, "Experiments in Molecular Genetics", (1972) Cold Spring Harbor Laboratory, Cold Spring Harbor, N.Y.), luciferase reporter (see, for example, J. Sambrook, "Molecular Cloning", (1989) Cold Spring Harbor Laboratory, Cold Spring Harbor, N.Y.), and the Green Fluorescent Protein (see, for example, M. Chalfie, *Photochem. Photobiol* (1995) 62(4), 651).

It is envisioned that the on-off switch effect of the present invention can be used in many ways, not necessarily limited to use with reporter genes. For example, the construct could be inserted into a nucleotide sequence as a switch to control the action of a gene encoding for a protein under investigation. In this way, it will be possible to determine the function of the protein by comparing the reaction of a cell or organism to the presence of and the absence of the protein. Alternatively, the promoter-operator-promoter switch could be placed upstream of any coding sequence regardless of function or nature. For instance, the end point may be a specific tRNA.

It is contemplated that the system of the present invention may be provided in the form of a kit. Such a kit would generally comprise at least two containers, the first container containing a polynucleotide molecule coding for a transrepressor fusion protein comprising a tet repressor and a transcription silencer protein domain, the second container containing a polynucleotide molecule comprising a tet operator sequence and at least two promoters, wherein at least one of the at least two promoters is capable of being ligated to a gene sequence coding for a protein.

While this invention has been described with reference to illustrative embodiments, this description is not intended to be construed in a limiting sense. Various modifications of the illustrative embodiments as well as other embodiments will be apparent to a person of skill in the art upon reference to this description. It is therefore contemplated that the appended claims will cover any such modifications or embodiments.

What is claimed is:

1. A polynucleotide molecule encoding a desired nucleic acid sequence to be expressed, said polynucleotide molecule being operably linked to a tet operator sequence and two promoters, which promoters are a thymidine kinase promoter of Herpes Simplex Virus and a human cytomegalovirus promoter.

2. The polynucleotide molecule of claim 1, wherein the desired nucleic acid sequence comprises a reporter gene.

3. The polynucleotide molecule of claim 2, wherein the desired nucleic acid sequence comprises a reporter gene selected from the group consisting of: a bacterial β-galactosidase gene, a chloramphenicol transferase reporter gene, a luciferase reporter gene, and a Green Fluorescent Protein gene.

4. The polynucleotide molecule of claim 2, wherein the reporter gene is a bacterial β-galactosidase gene.

5. The polynucleotide molecule of claim 1, wherein the tet operator sequence is a heptameric repeat of tetO.

6. The polynucleotide molecule of claim 1, wherein one of said promoters is positioned upstream of the tet operator sequence.

7. The polynucleotide molecule of claim 1, wherein said molecule is further operably linked to a nucleic acid sequence encoding a transrepressor fusion protein, consisting of a tet repressor and a transcription silencer protein domain.

8. The polynucleotide molecule of claim 7, wherein the transcription silencer protein domain is a highly conserved Kruppel-associated box domain of a Kox1 Zn-finger protein.

9. A vector comprising the polynucleotide molecule according to claim 1.

10. A eukaryotic cell transfected with:
   a first polynucleotide molecule encoding a desired nucleic acid sequence to be expressed, said first polynucleotide molecule being operably linked to a tet operator sequence and two promoters, which promoters are a thymidine kinase promoter of Herpes Simplex Virus and a human cytomegalovirus promoter; and
   a second polynucleotide molecule coding for a transrepressor fusion protein, consisting of a tet repressor and a transcription silencer protein domain.

11. The eukaryotic cell of claim 10, wherein the desired nucleic acid sequence includes a reporter gene selected from the group consisting of a bacterial β-galactosidase gene, a chloramphenicol transferase reporter gene, a luciferase reporter gene, and a Green Fluorescent Protein gene.

12. The eucaryotic cell of claim 10, wherein one of said promoters is positioned upstream of the tet operator sequence.

13. The eukaryotic cell of claim 10, wherein the first polynucleotide encoding a desired nucleic acid sequence to be expressed is operably linked to a nucleic acid sequence consisting of a Herpes Simplex Virus thymidine kinase promoter-heptameric tet operator-human cytomegalovirus promoter construct.

14. The eukaryotic cell of claim 10, wherein the second polynucleotide molecule coding for a transrepressor fusion protein comprises a tet repressor and a highly conserved Kruppel-associated box domain of a Kox1 Zn-finger protein.

15. A method for inducing the expression of the desired nucleic acid sequence of claim 10, comprising cultivating the eukaryotic cell of claim 10 in a medium comprising tetracycline or a tetracycline analogue.

16. A kit comprising two containers, the first container containing a first polynucleotide molecule coding for a transrepressor fusion protein, consisting of a tet repressor, and a transcription silencer protein domain, the second container containing a second polynucleotide molecule comprising a tet operator sequence and two promoters, which promoters are a thymidine kinase promoter of Herpes Simplex Virus and a human cytomegalovirus promoter, wherein said second polynucleotide molecule can be operably linked to a gene sequence coding for a protein.

17. The kit of claim 16 wherein the transcription silencer protein domain encodes a highly conserved Kruppel-associated box domain of a Kox1 Zn-finger protein.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Synthetic
      Primer

<400> SEQUENCE: 1

```
acgaggccct ttaagcttca agaattcctc                                          30

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Synthetic
      Primer

<400> SEQUENCE: 2
cagtaccgga atgccaagct tgca                                                24
```